(12) United States Patent
Kitamura

(10) Patent No.: US 8,969,627 B2
(45) Date of Patent: Mar. 3, 2015

(54) METHOD FOR PRODUCING 4,4'-DIFORMYLDIPHENYLALKANE

(75) Inventor: Mitsuharu Kitamura, Okayama (JP)

(73) Assignee: Mitsubishi Gas Chemical Company, Inc, Tokyo (JP)

( * ) Notice: Subject to any disclaimer, the term of this patent is extended or adjusted under 35 U.S.C. 154(b) by 0 days.

(21) Appl. No.: 14/008,162

(22) PCT Filed: Mar. 29, 2012

(86) PCT No.: PCT/JP2012/058440
§ 371 (c)(1),
(2), (4) Date: Dec. 11, 2013

(87) PCT Pub. No.: WO2012/133689
PCT Pub. Date: Oct. 4, 2012

(65) Prior Publication Data
US 2014/0094627 A1   Apr. 3, 2014

(30) Foreign Application Priority Data

Mar. 31, 2011 (JP) ................................. 2011-077942

(51) Int. Cl.
*C07C 45/49* (2006.01)
*C07C 47/544* (2006.01)

(52) U.S. Cl.
CPC ............. *C07C 47/544* (2013.01); *C07C 45/49* (2013.01)
USPC ......................................... 568/428; 568/429

(58) Field of Classification Search
CPC ................................ C07C 45/49; C07C 45/81
USPC ....................................................... 568/428
See application file for complete search history.

(56) References Cited

FOREIGN PATENT DOCUMENTS

| JP | 4-099744 A | 3/1992 |
| JP | 2535742 B2 | 7/1996 |
| JP | 2007-261991 A | 10/2007 |

OTHER PUBLICATIONS

International Search Report issued Jun. 19, 2012 in PCT/JP2012/058440.
Mutsuo Tanaka, et al., "Influence of Conformation and Proton-Transfer Dynamics in the Dibenzyl σ-Complex on Regioselectivity in Gattermann—Koch Formylation via Intracomplex Reaction" Journal of Organic Chemistry, vol. 63, No. 13, May 30, 1998, pp. 4408-4412.
Norihiko Yoneda, et al., "Studies in Organic Reaction Using Super Acids" Bulletin of the Faculty of Engineering, Hokkaido University, No. 91, Jul. 8, 1978, 17 Pages (with English language Abstract).
Sethuraman Sankararaman, et al., "Oxidative Carbon—Carbon Bond Cleavage of a [2.2]Paracyclophane Derivative—Efficient Intramolecular Trapping of the Radical Cation" European Journal of Organic Chemistry, No. 15, 2000, pp. 2711-2716.

*Primary Examiner* — Sikarl Witherspoon
(74) *Attorney, Agent, or Firm* — Oblon, Spivak, McClelland, Maier & Neustadt, L.L.P.

(57) ABSTRACT

A method for producing a 4,4'-diformyldiphenylalkane represented by the following formula (2), containing formylating a diphenylalkane represented by the following formula (1) with carbon monoxide in the presence of hydrogen fluoride and boron trifluoride, in which the reaction temperature of the formylation is from −50 to 5° C., from 5 to 30 mol of hydrogen fluoride is used per 1 mol of the diphenylalkane, and from 1.5 to 5 mol of boron trifluoride is used per 1 mol of the diphenylalkane:

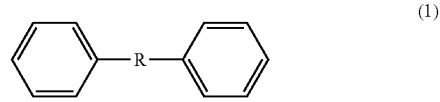

(1)

wherein R represents an alkanediyl group having from 1 to 6 carbon atoms,

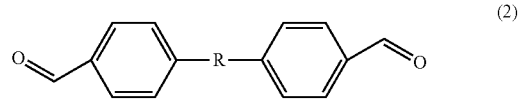

(2)

wherein R represents an alkanediyl group having from 1 to 6 carbon atoms.

10 Claims, No Drawings

METHOD FOR PRODUCING 4,4'-DIFORMYLDIPHENYLALKANE

TECHNICAL FIELD

The present invention relates to a method for producing a 4,4'-diformyldiphenylalkane with high purity, which is useful as various industrial chemical raw materials and production raw materials of medical drugs, agrichemicals, optical functional materials and electronic functional materials.

BACKGROUND ART

As an ordinary method for synthesizing a 4,4'-diformyldiphenylalkane, a method of formylation of a diphenylalkane and carbon monoxide with HF—$SbF_5$ as a catalyst has been known (see Patent Literature 1 and Non Patent Literature 1). However, Patent Literature 1 discloses that the yield of the 4,4'-diformyl compound (which may be hereinafter referred to as a 4,4'-compound) is 98%. Non Patent Literature 1 discloses that the yield of a diformyl is 97%, but the isomer ratio of the 4,4'-compound is as low as approximately 92%.

Non Patent Literature 2 discloses that $SbF_5$ is a viscous, colorless and transparent liquid, and has considerably strong corrosivity while it does not corrode glass.

A method of oxidation of [2.2]paracyclophane with molecular oxygen with $NOBF_4$ (nitrosonium fluoroborate) as a catalyst in a nitromethane/dichloromethane solvent has been known (see Non Patent Literature 3). However, the use of a large amount of the chloromethane solvent, which has a large environmental load, is practically difficult, the yield is as low as 30%, and there is a problem in availability of the raw material.

CITATION LIST

Patent Literature

Patent Literature 1: Japanese Patent No. 2,535,742

Non Patent Literature

Non Patent Literature 1: Tanaka, Mutsuo; Fujiwara, Masahiro; Xu, Qiang; Ando, Hisanori; Raeker, Todd J.; Journal of Organic Chemistry; vol. 63; nb. 13; (1998); p. 4408-4412

Non Patent Literature 2: Yoneda, Norihiko; Takahashi, Yukio; Fukuhara, Tsuyoshi; Tomita, Noboru; Suzuki, Akira; Bulletin of the Faculty of Engineering, Hokkaido University; No. 91 (1978); p. 3 (p. 55)

Non Patent Literature 3: Sankararaman, Sethuraman; Hopf, Henning; Dix, Ina; Jones, Peter G.; European Journal of Organic Chemistry; nb. 15; (2000); p. 2711-2716

SUMMARY OF INVENTION

Technical Problem

The HF—$SbF_5$ catalyst disclosed in Patent Literature 1 has a problem in handling and is difficult to apply to production methods used industrially. Specifically, $SbF_5$ has a viscous nature, and a pump suffers cavitation (generation of bubbles) in the portion with a high concentration thereof, which prevents a stable continuous operation.

$SbF_5$ does not corrode glass, but has strong hygroscopicity and generates hydrogen fluoride (HF) through severe reaction with water, which may easily corrode glass or the like. Accordingly, it is impossible to use in a glass vessel unless it is handled in an anhydrous state with sufficient caution. Furthermore, $SbF_5$ does not exhibit the catalytic action as it is, and thus is generally used necessarily in the form of a super-acid in combination with HF or sulfuric acid. Therefore, an HF—$SbF_5$ catalyst may corrode glass due to the presence of HF and thus disadvantageously has difficulty in handling.

While the complex decomposition of a substrate and a catalyst is generally achieved by the heat of a refluxing solvent, $SbF_5$ has a high boiling point of 141° C., which requires the use of a large amount of an inert solvent having a boiling point higher than that temperature, and thus the cost of the heat source is disadvantageously increased.

According to the method disclosed in Non Patent Literature 1, the yield of a diformyl compound is as good as 97% as described above, but the isomer ratio of a 4,4'-diformyl compound (which may be hereinafter referred to as a 4,4'-compound) is as low as approximately 92%, and the reaction solution contains, as isomer impurities, a 2,2'-diformyl compound (which may be hereinafter referred to as a 2,2'-compound) at a ratio of 5% and a 2,4'-diformyl compound (which may be hereinafter referred to as a 2,4'-compound) at a ratio of 3%. The isomer impurities have properties that are similar to those of the target 4,4'-compound and are difficult to be separated by crystallization or the like, and the impurities may impair the product value thereof as an optical functional material. Accordingly, the purity (isomer ratio) of the 4,4'-compound in the isomers containing the 4,4'-compound, the 2,2'-compound and the 2,4'-compound is preferably high.

Furthermore, for example, the purity of the 4,4'-compound (i.e., the purity of the 4,4'-compound in the final product) is preferably 90% or more when a 4,4'-diformyldiphenylalkane is used as an optical functional material. However, even though the 2,2'-compound and the 2,4'-compound are separated from the 4,4'-compound by multistage crystallization or the like, it is not an economical method unless the separated compounds are efficiently used. Accordingly, there is a demand for an effective selective synthesis method of a 4,4'-diformyldiphenylalkane based on reaction conditions.

Consequently, there is a demand for establishing a production method using a catalyst withstanding industrial use.

An object of the present invention is to provide an industrially advantageous production method of a 4,4'-diformyldiphenylalkane that is capable of providing an isomer ratio of a 4,4'-diformyl compound of 95% or more.

Solution to Problem

The present inventor has found that in a method of producing a 4,4'-diformyldiphenylalkane from a diphenylalkane and carbon monoxide, a 4,4'-diformyldiphenylalkane with a high isomer ratio is obtained by an industrially advantageous method by making the reaction temperature within a prescribed range, using hydrogen fluoride and boron trifluoride as catalysts, and making the ratios of the catalysts and the diphenylalkane within particular ranges, and thus completed the present invention. The present invention relates to the following.

[1] A method for producing a 4,4'-diformyldiphenylalkane represented by the following formula (2), containing formylating a diphenylalkane represented by the following formula (1) with carbon monoxide in the presence of hydrogen fluoride and boron trifluoride, a reaction temperature of the formylation being from −50 to 5° C., from 5 to 30 mol of hydrogen fluoride being used per 1 mol of the diphenylalkane, and from 1.5 to 5 mol of boron trifluoride being used per 1 mol of the diphenylalkane:

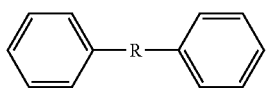

(1)

wherein R represents an alkanediyl group having from 1 to 6 carbon atoms,

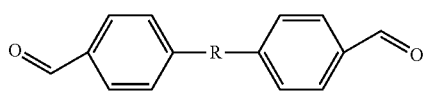

(2)

wherein R represents an alkanediyl group having from 1 to 6 carbon atoms.

[2] The method for producing a 4,4'-diformyldiphenylalkane according to the item [1], wherein the diphenylalkane is diphenylethane, and the 4,4'-diformyldiphenylalkane is 4,4'-diformyldiphenylethane.

[3] The method for producing a 4,4'-diformyldiphenylalkane according to the item [1], wherein the diphenylalkane is 1,3-diphenylpropane, and the 4,4'-diformyldiphenylalkane is 4,4'-diformyl-1,3-diphenylpropane.

[4] The method for producing a 4,4'-diformyldiphenylalkane according to any one of the items [1] to [3], wherein crystallization is performed after the formylation.

[5] The method for producing a 4,4'-diformyldiphenylalkane according to any one of the items [1] to [4], wherein the 4,4'-diformyldiphenylalkane thus produced has a purity of 90% or more.

Advantageous Effects of Invention

According to the present invention, an industrially advantageous production method of a 4,4'-diformyldiphenylalkane is provided that can provide an isomer ratio of the 4,4'-diformyl compound of 95% or more by using hydrogen fluoride and boron trifluoride as catalyst under the particular formylation conditions.

The present invention has the following advantageous effects as compared to the ordinary method using an HF—SbF$_5$ catalyst.

SbF$_5$ is a colorless, viscous and oily liquid having a melting point of 8.3° C. and a boiling point of 141° C., has strong hygroscopicity, generates HF through severe reaction with water, and easily corrodes glass or the like, as described above. Accordingly, a practical equipment using an HF—SbF$_5$ catalyst system becomes a significantly heavy process using an equipment formed of a special fluorine resin that is proven in laboratories, or the like.

In the present invention, on the other hand, such a heavy process is unnecessary, and BF$_3$ is in the form of gas and thus is easy in handling and practically excellent.

The practically excellent nature will be described in detail. The HF—SbF$_5$ catalyst has a higher acid strength than that of the HF—BF$_3$ catalyst according to the present invention, and it is thus expected that a stainless steel vessel may not be used therefor. Accordingly, initial investigations including material evaluation may be necessarily performed for achieving the practical equipment therefor, and thus there may be various problems in its practical application.

On the other hand, the HF—BF$_3$ catalyst according to the present invention has practically excellent points. For example, (1) practical equipments therefor have been developed the material evaluation of which has been variously made, and (2) the use of the HF—BF$_3$ catalyst enables a homogeneous liquid phase process.

Furthermore, the present invention is advantageous in the recovery method of the catalyst, as compared to the HF—SbF$_5$ catalyst. In the HF—SbF$_5$ catalyst, HF is necessarily cooled since it has a boiling point of 20° C., whereas SbF$_5$ is necessarily heated since it has a melting point of 8.3° C. Accordingly, it is considered that the catalyst system may have problems, such as clogging and purging outside the system, but the reaction conditions and the catalyst recovery method of the HF—BF$_3$ system in the present invention have been industrially established, and thus the catalyst system of the present invention is superior in industrial production.

DESCRIPTION OF EMBODIMENTS

The method for producing a 4,4'-diformyldiphenylalkane of the present invention is a method for producing a 4,4'-diformyldiphenylalkane represented by the following formula (2) by formylating a diphenylalkane represented by the following formula (1) with carbon monoxide in the presence of hydrogen fluoride (which may be hereinafter referred to as HF) and boron trifluoride (which may be hereinafter referred to as BF$_3$) as catalysts, as represented by the following formula.

According to the production method, a 4,4'-diformyldiphenylalkane may be obtained at an isomer ratio, for example, of 95% or more of the 4,4'-diformyl compound at a high yield. HF and BF$_3$ used as the catalysts have high volatility and can be recovered and reused. Accordingly, the used catalysts may not be discarded, and thus the production method is excellent in economy and simultaneously reduces the environmental load.

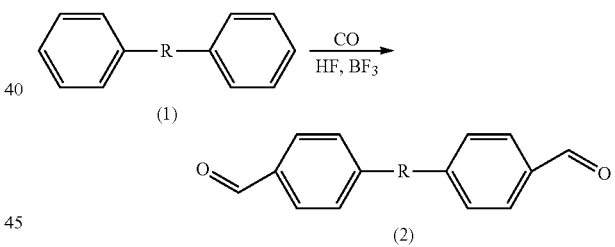

In the formulae (1) and (2), R represents an alkanediyl group having from 1 to 6 carbon atoms.

Examples of the diphenylalkane used in the present invention include diphenylmethane, diphenylethane, 1,3-diphenylpropane, 1,2-diphenylpropane, 1,4-diphenylbutane, 1,3-diphenylbutane, 1,2-diphenylbutane, 2,3-diphenylbutane, 1,5-diphenylpentane, 1,4-diphenylpentane, 1,3-diphenylpentane, 1,2-diphenylpentane, 2,4-diphenylpentane, 2,3-diphenylpentane, 1,6-diphenylhexane, 1,5-diphenylhexane, 1,4-diphenylhexane, 1,3-diphenylhexane, 1,2-diphenylhexane, 2,5-diphenylhexane, 2,4-diphenylhexane, 2,3-diphenylhexane or 2,3-dimethyl-2,3-diphenylbutane, and the production method thereof is not particularly limited and may be a method of separating it from a tar distillate or a petroleum distillate, a method of coupling a corresponding halide using a nickel-copper catalyst, or a method of alkylating a corresponding olefin and a corresponding alkylbenzene with a metallic sodium catalyst.

In the present invention, the reaction temperature of formylation is from −50 to 5° C., preferably from −50 to −10° C., more preferably from −40 to −10° C., and further preferably from −35 to −25° C. The reaction temperature exceeding 5° C. is not preferred since a polymerization product may be by-produced to decrease the yield. The temperature lower than −50° C. is not preferred since the formylation speed may be decreased.

The reaction time is preferably from 1 to 5 hours. When the reaction time is in the range, a sufficient diphenylalkane conversion may be obtained, and the possibility of deteriorating the efficiency due to increase of the equipment size for ensuring the residence time tends to be decreased.

The amount of $BF_3$ with respect to the diphenylalkane is from 1.5 to 5 mol, preferably from 2.5 to 5 mol, more preferably from 2.5 to 4 mol, and further preferably from 3 to 4 mol, per 1 mol of the diphenylalkane.

When the amount of $BF_3$ is less than 1.5 mol, the formylation reaction may be delayed. When the amount of $BF_3$ exceeds 5 mol, no further enhancement in yield may be obtained, but the sizes of the reactor and the $BF_3$ recovering device may be increased, which are not preferred from the standpoint of the production efficiency.

HF used in the present invention is preferably substantially anhydrous. The amount of HF with respect to the diphenylalkane is from 5 to 30 mol, preferably from 10 to 30 mol, more preferably from 10 to 25 mol, and further preferably from 15 to 25 mol, per 1 mol of the diphenylalkane.

When the amount of HF is less than 5 mol, the formylation reaction may not proceed efficiently. When the amount of HF exceeds 30 mol, no further enhancement in yield may be obtained, but the sizes of the reactor and the HF recovering device may be increased, which are not preferred from the standpoint of the production efficiency.

In the present invention, a reaction solvent that dissolves the diphenylalkane as a raw material and is inert to the diphenylalkane and the HF—$BF_3$, for example, a saturated aliphatic hydrocarbon, such as hexane, heptane and decane, may be used. In this case, the polymerization reaction may be further suppressed from occurring to enhance the yield, but the use or non-use thereof and the amount thereof may be appropriately selected since the use of a large amount of the solvent may cause decrease of the volume efficiency of the reaction and deterioration of the unit energy consumption required for separation.

The carbon monoxide used in the present invention may contain an inert gas, such as nitrogen and methane, and preferably has a carbon monoxide partial pressure of from 0.5 to 5 MPa, and more preferably from 1 to 3 MPa.

When the carbon monoxide partial pressure is from 0.5 to 5 MPa, the formylation reaction may proceed sufficiently, and the amount of the monoformylation reaction product may be decreased. Furthermore, the occurrence of the side reactions, such as isomerization and polymerization, may be suppressed to reduce decrease of the yield. Moreover, it is also preferred from the standpoint of the reaction efficiency and the cost.

The reaction mode of the formylation reaction in the method of the present invention is not particularly limited as far as it includes an agitation method capable of mixing a liquid phase and a gas phase sufficiently, and any of a batch system, a semi-batch system and a continuous system may be employed.

In a batch system, for example, a diphenylalkane dissolved in a solvent and prescribed amounts of anhydrous HF and $BF_3$ are charged in an autoclave equipped with a electromagnetic agitator; the contents are agitated and maintained at a liquid temperature from −50 to 5° C.; then the pressure is increased with carbon monoxide to from 0.5 to 5 MPa; the reaction solution is maintained at the pressure and the liquid temperature for from 1 to 5 hours until carbon monoxide is not absorbed; then the reaction solution is placed into ice; and the oily phase is collected and analyzed by gas chromatography, thereby confirming the formation of the 4,4'-diformyldiphenylalkane.

In a semi-batch system, prescribed amounts of anhydrous HF and $BF_3$ are charged in an autoclave equipped with a electromagnetic agitator; the contents are agitated and set to a liquid temperature from −50 to 5° C., which is maintained constant; then the pressure is increased with carbon monoxide to from 0.5 to 5 MPa; and carbon monoxide is prepared to be supplied to maintain the pressure constant. Thereafter, a diphenylalkane dissolved in a solvent is charged thereto; after charging, the reaction solution is maintained at that state for from 1 to 5 hours; then the reaction solution is placed into ice; and the oily phase is collected and analyzed by gas chromatography, thereby confirming the formation of the 4,4'-diformyldiphenylalkane.

In a continuous system, prescribed amounts of anhydrous HF and $BF_3$ are charged in an autoclave equipped with a electromagnetic agitator; the contents are agitated and set to a liquid temperature from −50 to 5° C., which is maintained constant; then the pressure is increased with carbon monoxide to from 0.5 to 5 MPa; and carbon monoxide is prepared to be supplied to maintain the pressure constant. Thereafter, semi-batch reaction is performed by supplying a diphenylalkane dissolved in a solvent. Subsequently, anhydrous HF and $BF_3$ are also supplied, and the reaction product solution is continuously withdrawn to iced water. The residence time of the reaction solution in the autoclave is preferably from 1 to 5 hours. When the residence time is 1 hour or more, the reaction tends to proceed sufficiently, and when it is 5 hour or less, the possibility of deteriorating the efficiency due to increase of the equipment size for ensuring the residence time tends to be decreased.

The resulting oily phase is analyzed by gas chromatography, thereby confirming the formation of the 4,4'-diformyldiphenylalkane.

The end point of the reaction may not be particularly limited, and for example, the time when the absorption of carbon monoxide is terminated may be designated as the end point.

The reaction product solution obtained through the formylation reaction is an HF solution of a 4,4'-diformyldiphenylalkane-HF—$BF_3$ complex, and the bond between the 4,4'-diformyldiphenylalkane and the HF—$BF_3$ is decomposed by heating to gasify and separate HF and $BF_3$, which may be recovered and reused. The decomposition operation of the complex is necessarily performed as quickly as possible to prevent the products from suffering deterioration by heat, isomerization, and the like. For performing the thermal decomposition of the complex quickly, it is preferred to decompose the complex under reflux, for example, of a solvent that is inert to HF—$BF_3$, such as a saturated aliphatic hydrocarbon, e.g., heptane, or an aromatic hydrocarbon, e.g., benzene.

There are cases where the thermal decomposition processed solution having been diluted with a large amount of solvent may contain a slight amount of HF. Thus the solution is neutralized and rinsed with a 0.5% sodium hydroxide aqueous solution, and then can be easily purified by removing the diphenylalkane as a raw material and a monoformyldiphenylalkane in ordinary distillation and crystallization process, thereby providing the a 4,4'-diformyldiphenylalkane with a purity of 90% or more as a product.

In the case where the 4,4'-diformyldiphenylalkane-HF—$BF_3$ complex is withdrawn into iced water, a solvent, such as 4-methyl-2-pentanone, 2,4-dimethyl-3-pentanone, 2-ethyl-1-hexanol, 3-methyl-3-octanol or dibutyl ether, is added thereto for dissolving the 4,4'-diformyldiphenylalkane in the form of solid, and then the solution is neutralized and rinsed with a 0.5% sodium hydroxide aqueous solution and then rinsed with warm water at 50° C. to dissolve the product in the oily phase. Thereafter, by cooling the oily phase to room temperature, the product is deposited while the unreacted raw material and the monoformyl compound as the intermediate remain in the oily phase, and the product is easily purified by filtration. Thus, a 4,4'-diformyldiphenylalkane with a purity of 90% or more may be obtained as a final product. In the case where the product has a poor isomer ratio after the reaction, the product may be necessarily subjected to purification by crystallization several times for providing a purity of 90% or more.

EXAMPLES

The method of the present invention will be described in more detail with reference to examples below, but the present invention is not limited to the examples. The evaluations were performed by the following manners.
(1) Gas Chromatography Analysis Conditions The gas chromatography was performed by using GC-17A, produced by Shimadzu Corporation, and as a capillary column HR-1 (0.32 mm in diameter×25 m), produced by Shinwa Chemical Industries Ltd. The temperature rise condition was 5° C. per min from 100° C. to 320° C.
(2) Isomer Ratio, Purity of 4,4'-Compound, and Isolated Yield The product was analyzed by gas chromatography to obtain the area ratios of the monoformyl compound and the diformyl compounds (i.e., the 4,4-compound, the 2,2'-compound and the 2,4'-compound) of the product, and the isomer ratios and the purity of the 4,4'-compound were calculated by the following expressions.

Isomer ratio (%)=(4,4'-compound)/((4,4'-compound)+(2,2'-compound)+(2,4'-compound))×100

Purity of 4,4'-compound (%)=(4,4'-compound)/((mono-compound)+(4,4'-compound)+(2,2'-compound)+(2,4'-compound)+other components (*LE*+raw material+*HE*))×100

In the expression, LE means the components having a low boiling point compared to the raw material, and HE means the components having a high boiling point compared to the raw material except for the monoformyl compound and the diformyl compounds as the product.

Isolated yield (% by mol)=((collected amount of 4,4'-diformyldiphenylalkane as the product)/(molecular weight of 4,4'-diformyldiphenylalkane))/((charged amount of diphenylalkane as the raw material)/(molecular weight of diphenylalkane as the raw material))×100

Example 1

Production of 4,4'-Diformyl-1,2-diphenylethane by Formylation of Diphenylethane (see Formula (3) below)

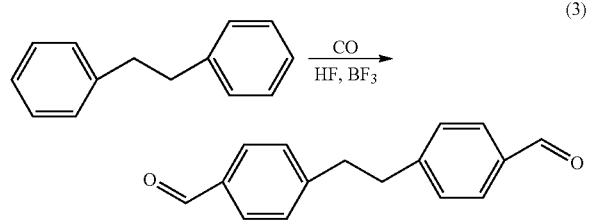

(3)

50.1 g (0.275 mol) of diphenylethane (produced by Tokyo Kasei Kogyo Co., Ltd.), 50.1 g of n-heptane, 110.0 g (5.497 mol) of anhydrous HF and 65.2 g (0.962 mol) of $BF_3$ were charged in a stainless steel autoclave, which was equipped with a knuckle drive agitator, three inlet nozzles at the upper portion and one outlet nozzle at the lower portion, and had a jacket capable of controlling the internal temperature thereof while the contents were agitated and the liquid temperature was maintained at −30° C., the pressure was increased with carbon monoxide to 2 MPa. Thereafter, the reaction was performed while the pressure was maintained at 2 MPa and the liquid temperature was maintained at −30° C. for 1 hour, and then the reaction product solution was placed in ice and neutralized. A solid matter obtained through the neutralization was analyzed by gas chromatography to obtain reaction results, which revealed that the diphenylethane conversion was 99.4%, the yield of 4-formyl-1,2-diphenylethane was 23.6%, the yield of 4,4'-diformyl-1,2-diphenylethane was 72.9%, and the isomer ratio of 4,4'-diformyl-1,2-diphenylethane was 96.6%.

300 g of 4-methyl-2-pentanone was added to the solid matter thus obtained, and the resulting solution was neutralized once with 100 mL of a 0.5% sodium hydroxide aqueous solution and rinsed twice with 100 mL of warm water at 50° C. to dissolve the product in the oily phase. The oily phase was then spontaneously cooled to room temperature to deposit a solid matter, which was collected by filtration, thereby providing 35.1 g of a white solid matter having a 4,4'-diformyl-1,2-diphenylethane purity of 95.7% (isolated yield: 53.5%, diphenylethane basis).

Example 2

The formylation reaction and the treatment of the reaction product solution were performed in the same manner as in Example 1 except that the reaction time was changed to 3 hours. A solid matter thus obtained was analyzed by gas chromatography to obtain reaction results, which revealed that the diphenylethane conversion was 99.6%, the yield of 4-formyl-1,2-diphenylethane was 10.9%, the yield of 4,4'-diformyl-1,2-diphenylethane was 84.2%, and the isomer ratio of 4,4'-diformyl-1,2-diphenylethane was 95.8%. The purification by crystallization was performed in the same manner as in Example 1, thereby providing 46.6 g of a white solid matter having a 4,4'-diformyl-1,2-diphenylethane purity of 95.5% (isolated yield: 71.2%, diphenylethane basis).

Example 3

The formylation reaction and the treatment of the reaction product solution were performed in the same manner as in Example 1 except that the charged amount of $BF_3$ was changed to 46.6 g (0.687 mol). A solid matter thus obtained was analyzed by gas chromatography to obtain reaction results, which revealed that the diphenylethane conversion was 76.1%, the yield of 4-formyl-1,2-diphenylethane was 18.0%, the yield of 4,4'-diformyl-1,2-diphenylethane was 55.9%, and the isomer ratio of 4,4'-diformyl-1,2-diphenylethane was 96.2%. The purification by crystallization was performed in the same manner as in Example 1, thereby providing 20.4 g of a white solid matter having a 4,4'-diformyl-1,2-diphenylethane purity of 95.3% (isolated yield: 31.2%, diphenylethane basis).

Example 4

The formylation reaction and the treatment of the reaction product solution were performed in the same manner as in Example 3 except that the charged amount of anhydrous HF was changed to 82.5 g (4.123 mol). A solid matter thus obtained was analyzed by gas chromatography to obtain reaction results, which revealed that the diphenylethane conversion was 75.4%, the yield of 4-formyl-1,2-diphenylethane was 21.1%, the yield of 4,4'-diformyl-1,2-diphenylethane was 52.1%, and the isomer ratio of 4,4'-diformyl-1,2-diphenylethane was 96.3%. The purification by crystallization was performed in the same manner as in Example 1, thereby providing 17.8 g of a white solid matter having a 4,4'-diformyl-1,2-diphenylethane purity of 95.1% (isolated yield: 27.1%, diphenylethane basis).

Example 5

The formylation reaction and the treatment of the reaction product solution were performed in the same manner as in Example 4 except that the reaction temperature was changed to 0° C. A solid matter thus obtained was analyzed by gas chromatography to obtain reaction results, which revealed that the diphenylethane conversion was 98.7%, the yield of 4-formyl-1,2-diphenylethane was 53.1%, the yield of 4,4'-diformyl-1,2-diphenylethane was 42.1%, and the isomer ratio of 4,4'-diformyl-1,2-diphenylethane was 95.5%. The purification by crystallization was performed in the same manner as in Example 1, thereby providing 11.8 g of a white solid matter having a purity of 92.4% (isolated yield: 18.0%, diphenylethane basis).

The yield was lowered due to the high reaction temperature, and 4-formyl-1,2-diphenylethane as an intermediate contaminated the product, thereby failing to provide 4,4'-diformyl-1,2-diphenylethane having a 4,4'-diformyl-1,2-diphenylethane purity of 95% or more.

Example 6

The formylation reaction and the treatment of the reaction product solution were performed in the same manner as in Example 4 except that the charged amount of anhydrous HF was changed to 41.3 g (2.060 mol). A solid matter thus obtained was analyzed by gas chromatography to obtain reaction results, which revealed that the diphenylethane conversion was 65.2%, the yield of 4-formyl-1,2-diphenylethane was 25.8%, the yield of 4,4'-diformyl-1,2-diphenylethane was 37.8%, and the isomer ratio of 4,4'-diformyl-1,2-diphenylethane was 96.6%.

The purification by crystallization was performed in the same manner as in Example 1, thereby providing 9.4 g of a white solid matter having a 4,4'-diformyl-1,2-diphenylethane purity of 94.6% (isolated yield: 14.3%, diphenylethane basis).

The purity was low due to the small amount of HF used.

Example 7

The formylation reaction and the treatment of the reaction product solution were performed in the same manner as in Example 4 except that the charged amount of $BF_3$ was changed to 37.3 g (0.549 mol). A solid matter thus obtained was analyzed by gas chromatography to obtain reaction results, which revealed that the diphenylethane conversion was 58.2%, the yield of 4-formyl-1,2-diphenylethane was 15.0%, the yield of 4,4'-diformyl-1,2-diphenylethane was 40.9%, and the isomer ratio of 4,4'-diformyl-1,2-diphenylethane was 96.1%.

The purification by crystallization was performed in the same manner as in Example 1, thereby providing 11.0 g of a white solid matter having a purity of 94.8% (isolated yield: 16.7%, diphenylethane basis).

The purity was low due to the small amount of $BF_3$ used.

Example 8

Production of 4,4''-Diformyl-1,3-diphenylpropane by Formylation of 1,3-Diphenylpropane (see Formula (4) below)

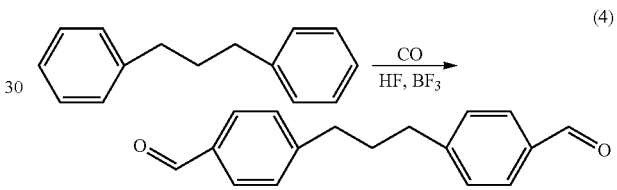

The formylation reaction and the treatment of the reaction product solution were performed in the same manner as in Example 1 except that 54.0 g (0.275 mol) of 1,3-diphenylpropane (produced by Tokyo Kasei Kogyo Co., Ltd.) was used as the raw material. A solid matter thus obtained was analyzed by gas chromatography to obtain reaction results, which revealed that the 1,3-diphenylpropane conversion was 97.2%, the yield of 4-formyl-1,3-diphenylpropane was 2.7%, the yield of 4,4'-diformyl-1,3-diphenylpropane was 91.0%, and the isomer ratio of 4,4'-diformyl-1,3-diphenylpropane was 97.4%. The purification by crystallization was performed in the same manner as in Example 1, thereby providing 59.1 g of a white solid matter having a 4,4'-diformyl-1,3-diphenylethane purity of 97.3% (isolated yield: 85.1%, diphenylpropane basis).

The reaction conditions, the reaction results and the final results of Examples are shown below.

TABLE 1

| | Reaction condition | | | | | Reaction results | | | | | | | | Final results | |
|---|---|---|---|---|---|---|---|---|---|---|---|---|---|---|---|
| Run | Time h | Temperature ° C. | HF/diphenylalkane mol ratio | $BF_3$/diphenylalkane mol ratio | LE | Raw material | Monocompound | 2,2'-compound | 2,4'-compound | 4,4'-compound | HE | Conversion (mol %) | Isomer ratio of 4,4'-compound (%) | Isolated yield (mol %) | Purity of 4,4'-compound (%) |
| | | | | | | | (% by GC) | | | | | | | | |
| Example 1 | 1 | −30 | 20.0 | 3.5 | 0.0 | 0.6 | 23.6 | 2.2 | 0.4 | 72.9 | 0.2 | 99.4 | 96.6 | 53.5 | 95.7 |
| Example 2 | 3 | −30 | 20.0 | 3.5 | 0.0 | 0.4 | 10.9 | 3.2 | 0.5 | 84.2 | 0.8 | 99.6 | 95.8 | 71.2 | 95.5 |
| Example 3 | 1 | −30 | 20.0 | 2.5 | 0.0 | 23.9 | 18.0 | 1.9 | 0.3 | 55.9 | 0.1 | 76.1 | 96.2 | 31.2 | 95.3 |
| Example 4 | 1 | −30 | 15.0 | 2.5 | 0.0 | 24.6 | 21.1 | 1.7 | 0.3 | 52.1 | 0.2 | 75.4 | 96.3 | 27.1 | 95.1 |
| Example 5 | 1 | 0 | 15.0 | 2.5 | 0.0 | 1.3 | 53.1 | 1.3 | 0.7 | 42.1 | 1.5 | 98.7 | 95.5 | 18.0 | 92.4 |
| Example 6 | 1 | −30 | 7.5 | 2.5 | 0.1 | 34.8 | 25.8 | 1.1 | 0.2 | 37.8 | 0.2 | 65.2 | 96.6 | 14.3 | 94.6 |

TABLE 1-continued

| | Reaction condition | | | | Reaction results | | | | | | | | Final results | |
|---|---|---|---|---|---|---|---|---|---|---|---|---|---|---|
| Run | Time h | Temperature °C. | HF/diphenylalkane mol ratio | BF$_3$/diphenylalkane mol ratio | LE | Raw material | Monocompound | 2,2'-compound (% by GC) | 2,4'-compound | 4,4'-compound | HE | Conversion (mol %) | Isomer ratio of 4,4'-compound (%) | Isolated yield (mol %) | Purity of 4,4'-compound (%) |
| Example 7 | 1 | −30 | 15.0 | 2.0 | 0.1 | 41.8 | 15.0 | 1.4 | 0.2 | 40.9 | 0.5 | 58.2 | 96.1 | 16.7 | 94.8 |
| Example 8 | 1 | −30 | 20.0 | 3.5 | 0.3 | 2.8 | 2.7 | 2.3 | 0.2 | 91.0 | 0.8 | 97.2 | 97.4 | 85.1 | 97.3 |

INDUSTRIAL APPLICABILITY

A 4,4'-diformyldiphenylalkane that is obtained by the industrially advantageous method according to the present invention has an isomer ratio of 95% or more and provides a 4,4'-diformyl compound with a high isolated purity only by one time crystallization, and therefore the 4,4'-diformyldiphenylalkane is useful as various industrial chemical raw materials and production raw materials of medical drugs, agrichemicals, optical functional materials and electronic functional materials.

The invention claimed is:

1. A method for producing a 4,4'-diformyldiphenyl alkane, the method comprising formylating a diphenylalkane represented by the following formula (1) with carbon monoxide in the presence of hydrogen fluoride and boron trifluoride:

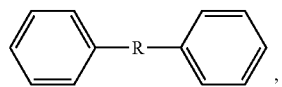
(1)

to form a 4,4'-diformyldiphenylalkane represented by formula (2):

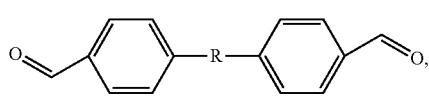
(2)

wherein:
a reaction temperature of the formylation is from −35 to −25° C.;
from 5 to 30 mol of the hydrogen fluoride per 1 mol of the diphenylalkane is present;
from 1.5 to 5 mol of the boron trifluoride per 1 mol of the diphenylalkane is present; and
R represents an alkanediyl group having from 1 to 6 carbon atoms.

2. The method according to claim 1, wherein the diphenylalkane is diphenylethane, and the 4,4'-diformyldiphenylalkane is 4,4'-diformyldiphenylethane.

3. The method according to claim 1, wherein the diphenylalkane is 1,3-diphenylpropane, and the 4,4'-diformyldiphenylalkane is 4,4'-diformyl-1,3-diphenylpropane.

4. The method according to claim 1, further comprising crystallization after the formylation.

5. The method according to claim 1, wherein the 4,4'-diformyldiphenylalkane produced has a purity of 90% or more.

6. The method according to claim 2, further comprising crystallization after the formylation.

7. The method according to claim 3, further comprising crystallization after the formylation.

8. The method according to claim 2, wherein the 4,4'-diformyldiphenylalkane produced has a purity of 90% or more.

9. The method according to claim 3, wherein the 4,4'-diformyldiphenylalkane produced has a purity of 90% or more.

10. The method according to claim 4, wherein the 4,4'-diformyldiphenylalkane produced has a purity of 90% or more.

* * * * *